US008697043B1

(12) United States Patent
Ter-Antonyan et al.

(10) Patent No.: US 8,697,043 B1
(45) Date of Patent: Apr. 15, 2014

(54) ODOR SUPPRESSION OF VOLATILE ORGANIC ANALGESIC COMPOUNDS AND METHOD OF USE

(71) Applicant: Chattem, Inc., Chattanooga, TN (US)

(72) Inventors: Vardan Ter-Antonyan, Chattanooga, TN (US); Jason Sondgeroth, Chattanooga, TN (US); David Jaeger, Chattanooga, TN (US); Shane Smith, Chattanooga, TN (US); Elisa Barnes, Chattanooga, TN (US)

(73) Assignee: Chattem, Inc., Chattanooga, TN (US)

( * ) Notice: Subject to any disclaimer, the term of this patent is extended or adjusted under 35 U.S.C. 154(b) by 0 days.

(21) Appl. No.: 13/736,454

(22) Filed: Jan. 8, 2013

(51) Int. Cl.
*A61L 9/00* (2006.01)
*A61L 9/01* (2006.01)
*A61L 9/04* (2006.01)
*A61K 31/045* (2006.01)
*C07C 35/00* (2006.01)

(52) U.S. Cl.
USPC ........ 424/76.1; 424/76.2; 424/76.3; 514/739; 586/875

(58) Field of Classification Search
None
See application file for complete search history.

(56) References Cited

U.S. PATENT DOCUMENTS

| | | | |
|---|---|---|---|
| 4,316,887 A | 2/1982 | Kamishita | |
| 5,741,510 A | 4/1998 | Rolf | |
| 5,866,157 A | 2/1999 | Higo | |
| 6,579,543 B1 | 6/2003 | McClung | |
| 7,034,083 B2 | 4/2006 | Yasukochi et al. | |
| 2002/0192273 A1 | 12/2002 | Buseman | |
| 2004/0001891 A1* | 1/2004 | Smith et al. | 424/469 |
| 2004/0228803 A1 | 11/2004 | Smith | |
| 2007/0142317 A1 | 6/2007 | Warren | |
| 2008/0286320 A1 | 11/2008 | Vega | |
| 2010/0150971 A1 | 6/2010 | Seidling | |
| 2011/0305657 A1 | 12/2011 | Kuper | |
| 2011/0319399 A1 | 12/2011 | Miura | |
| 2012/0128744 A1* | 5/2012 | Sorge et al. | 424/401 |
| 2012/0129937 A1 | 5/2012 | Issleib | |

FOREIGN PATENT DOCUMENTS

EP 1238664 B1 2/2007

OTHER PUBLICATIONS

Iowa State, Section 9—Physical and Chemical Properties, http://avogadro.chem.iastate.edu/MSDS/camphor.html, Jul. 20, 2012, p. 3.

Wikipedia, Camphor, http://en.wikipedia.org/wiki/Camphor, Aug. 15, 2012.
Wikipedia, Menthol, http://en.wikipedia.org/wiki/Menthol, Aug. 15, 2012.
UNEP Publications, SIDS Initial Assessment Report for SIAM 16, OECD SIDS, May 27-30, 2003, Paris, France.
Wikipedia, Farnesol, http://en.wikipedia.org/wiki/Farnesol, Aug. 15, 2012.
Symrise Cosmetic Ingredients Marketing, Farnesol "A Natural and Selective Bacteriostat", Feb. 20, 2003.
IFRA RIFM, IFRA RIFM QRA Information Booklet Version 5.0, Revised Jun. 7, 2010.
Symrise, Active Ingredients SymSitive® 1609 399944, A New Generation of Active Ingredients for Fast Skin Relief, http:///www.happi.com/news/2009/11/05/fast_skin_relief_with_symsitive_1609, Jul. 20, 2012.
Scientific Committee on Consumer Products (SCCP), Opinion on Dermal Sensitisation Quantitative Risk Assessment (Citral, Farnesol and Phenylacetaldehyde), Jun. 24, 2008, p. 15, Health & Consumer Protection Directorate-General of the Euopean Commission.
Lubrizol Advanced Materials, Inc., Novemer™ EC-2 Polymer, Multifunctional Liquid Polymer for High Performance Skin Care Systems; TechnicatData Sheet TDS-792, Aug. 26, 2011.
Nicoletta Galeotti, Lorenzo Di Cesare Mannelli, Gabriela Mazzanti, Alessandro Bartolini, Carla Ghelardini, Menthol: a natural analgesic compound, Neuroscience Letters, Apr. 12, 2002, vol. 322, Issue 3, pp. 145-148; http://www.sciencedirect.com/science/article/pii/S0304394001025277, Feb. 15, 2012.
K.R. Brain, D.M. Green, P.J. Dykes, R. Marks, T.S. Bola, The Role of Menthol in Skin Penetration from Topical Formulations of Ibuprofen 5% in vivo, Skin Pharmacology and Physiology, Journal of Pharmacological and Biophysical Research, 2006, vol. 19, No. 1, pp. 17-21; http://content.karger.com/produktedb.asp?typ=pdf&file=SPP2006019001017, Feb. 15, 2012.
Gil Yosipovitch, Christiane Szolar, Xiao Ying Hui, Howard Maibach, Effect of topically applied Methol on thermal, pain and itch sensations and biophysical properties of the skin, Archives of Dermatological Research, 1996, vol. 288, Nos. 5-6, pp. 245-248; http://www.springerlink.com/content/y8m00473h474kvu4/, Feb. 15, 2012.

* cited by examiner

*Primary Examiner* — Robert A Wax
*Assistant Examiner* — Jeffrey T Palenik
(74) *Attorney, Agent, or Firm* — Miller & Martin PLLC

(57) ABSTRACT

Disclosed are odor suppressing analgesic compositions comprising:
a) from about 0.1% to about 20%, by weight, of farnesol or other suitable deodorizing bacteriostatic agent; and
b) from about 0.1% to about 60%, by weight, volatile organic compound wherein said volatile organic compound may be encapsulated and is chosen from the following (menthol, camphor, methyl salicylate, methyl nicotiniate, or combination of thereof); and
c) a water-in-oil or oil-in-water emulsion, gel, patch, plaster, ointment, solution or spray carrier. An optimized odor suppressing analgesic composition can provide a combination of antimicrobial properties, odor suppression properties, skin cooling or heating properties, topical analgesic properties, low irritation and stability.

20 Claims, 2 Drawing Sheets

ODOR SUPPRESSION OF VOLATILE ORGANIC ANALGESIC COMPOUNDS AND METHOD OF USE

FIELD OF THE INVENTION

The present invention relates to odor suppression technologies to substantially suppress or block the odor of volatile organic compounds (VOCs), and most particularly the odor of menthol and camphor.

BACKGROUND OF THE INVENTION

In the field of topical analgesics, pain relieving formulations must either be extensively tested and individually approved by the Food & Drug Administration ("FDA"), or conform to the requirements of the FDA's over-the counter monograph. The two principal odorless topical analgesic active ingredients approved for use under the FDA's monograph are capsaicin and trolamine salicylate. Capsaicin is the principal capsaicinoid in chili peppers and it activates heat and pain sensing neurons producing a burning sensation when applied to the skin. Prolonged activation of these neurons by capsaicin depletes presynaptic substance P, one of the body's neurotransmitters for pain and heat. The result appears to be that the chemical mimics a burning sensation, the nerves are overwhelmed by the influx, and are unable to report pain for an extended period of time. While the result is an effective form of pain relief for some people, many people do not readily tolerate exposure to capsaicin.

Trolamine salicylate is used as a topical pain reliever to reduce swelling and inflammation. Trolamine salicylate is not tolerated by people with allergies to salicylates such as aspirin (salicylic acid), and the FDA has indicated that trolamine salicylate will be excluded from the Final Monograph for External Analgesic Drug Products for Over-the-Counter Human Use (21 CFR part 348).

As a result, there is a need for an efficacious and odorless topical analgesic product that utilizes an FDA OTC monograph active topical analgesic ingredient. It is well known that one of the most efficacious topical analgesics in the OTC monograph is menthol, in a concentration from 1.25%-16%, but menthol has a distinct and strong odor. Camphor, in a concentration from 3%-11%, is another topical analgesic from the OTC Monograph, but it also has a strong odor. At present the odorless topical analgesic products on the market utilize trolamine salicylate, capsaicin, or the homeopathic active ingredient arnica montana. These alternatives are not adequate because trolamine salicylate will soon be excluded from the FDA OTC Monograph, capsaicin is not universally tolerated, and there are controversial and mixed results about the efficacy of homeopathic actives in topical pain relief. Methyl salicylate at high concentrations, 10-60%, may also be used under the OTC Monograph, and has a strong wintergreen odor that may need suppression for acceptable use in public situations. Methyl nicotinate is another approved external analgesic ingredient, at concentrations of 0.25-1.0%, but possesses a sweet, herbaceous, tobacco-like odor that can often be masked rather than suppressed.

Odor suppression has always been problematic, especially with products containing menthol and camphor. Previously, the odor of menthol and camphor has been masked with other fragrances, but not truly suppressed or blocked. For example the odor of a product containing 7-8% menthol could be masked or altered with essential oils like spearmint, grapefruit oil, tea tree and such. The odor of a product containing both a significant amount of menthol and camphor could be masked or altered by including essential oils like spearmint, grapefruit oil, lemon oil, cucumber oil, thyme and such. The issue with odor from products containing camphor and menthol comes from the fact that these two compounds have a very high volatility and instead of reducing or stopping these compounds from volatilizing, the essential oils or other compounds were introduced only to alter or mask the odor. There has previously been no effective technique to reduce the odor of menthol or camphor containing products by actually reducing the volatility of the ingredients.

SUMMARY OF THE INVENTION

The invention utilizes a combination of ingredients to produce a safe and efficacious topical analgesic so that one or both of menthol and camphor may be included among the active ingredients, and little or no resulting odor. A first step to achieving odor reduction is the addition of a deodorizing bacteriostatic agent. A preferred agent of this type is farnesol, which is widely available. Farnesol has a long history of use in perfumery and fragrances to enhance floral scents and in cosmetic products as a deodorant because of its anti-bacterial activity. Farnesol's stated method of action for enhancing perfume scents is as a co-solvent that regulates volatility of the odorants. However, farnesol has not been used to address the problem of strong odor of topical analgesics containing the active amount of menthol, camphor or similar volatile organic compounds (VOCs). Two apparent reasons for this are that farnesol has tended to enhance sweet and lilac floral notes in perfumes, and because farnesol can be irritating or cause an allergic reaction if used in significant amounts or by people who are sensitive or allergic to fragrance in general. In fact, the International Fragrance Association limits concentrations of farnesol to less than 1% for most applications involving sustained contact to the skin. The Scientific Committee on Consumer Products of the European Commission set upper limits for farnesol concentrations in various products ranging from 0.11% in deodorants to a maximum of 1.2% in hydroalcoholic products for use on unshaved skin. Other deodorizing bacteriostatic agents could include 2-methyl-5-cyclohexyl pentanol and dimethyl phenyl 2-butanol, however, they lack the odor suppressing efficacy and relatively low cost of farnesol.

Initial attempts to use farnesol to modify topical analgesic odor were not particularly successful when using amounts as small as 1%. However, modifications to product formulation and the addition of greater amounts of farnesol produced noticeable reductions in menthol and camphor odor. At these concentrations of farnesol exceeding 1%, however, the risk of irritation and sensitization to farnesol are not acceptable for routine use.

Rather than reject the use of farnesol in concentrations over 1%, an attempt was made to reduce the tendency of farnesol to cause irritation or reaction. A neuro-sensorial ingredient is therefore added to the formulation to address the irritation, sensitization and allergies related to significant levels of farnesol. A commercially available product, SymSitive 1609 from Symrise, with a principal active ingredient of 4-t-butyl-cyclohexanol, has been identified as particularly suitable for this purpose even at low concentrations.

However, experimentation has shown that moderate concentrations of farnesol, in the range of about 2-6%, does not independently reduce the volatility of menthol and camphor sufficiently to nearly eliminate the associated odor in water and alcohol base formulations. Two additional steps can be taken to reduce odor. One step is the use of encapsulated VOCs, like encapsulated menthol or encapsulated camphor.

While this is believed to provide additional odor reduction by virtue of the encapsulation, encapsulated VOC's actually contain significant amounts of non-volatile encapsulation material so that the absolute amounts of menthol or camphor are also reduced.

A second step to further minimize odor is the optimization of the formulation of analgesic mixtures containing menthol and/or camphor. In this fashion, the ratios of ingredients are selected so that after mixing with solvents and surfactants, there are relatively small free amounts of the VOCs. When formulated in this fashion, farnesol is added late in the formulation process, generally after emulsification of the carrier, and in this case moderate levels of farnesol are sufficient to reduce the volatility of the remaining free amounts of VOCs and nearly eliminate odor.

The advantages and benefits of this invention over known art can include one or more of the following:

1. Enables formulation of safe, efficacious and odorless topical analgesic products without using trolamine salicylate, capsaicin, or homeopathic actives as currently practiced.
2. Uses a neuro-sensorial ingredient to prevent skin irritation or allergic reaction from farnesol.
3. Contains no parabens or other preservatives because it is well self-preserved.
4. Contains farnesol, an organic compound that reduces the volatility of the topical analgesic actives, supresses their odor and preserves the product.

DESCRIPTION OF THE DRAWINGS

Certain aspects of the invention can be appreciated with reference to the following drawings in which.

DETAILED DESCRIPTION OF THE INVENTION

Figure 1:
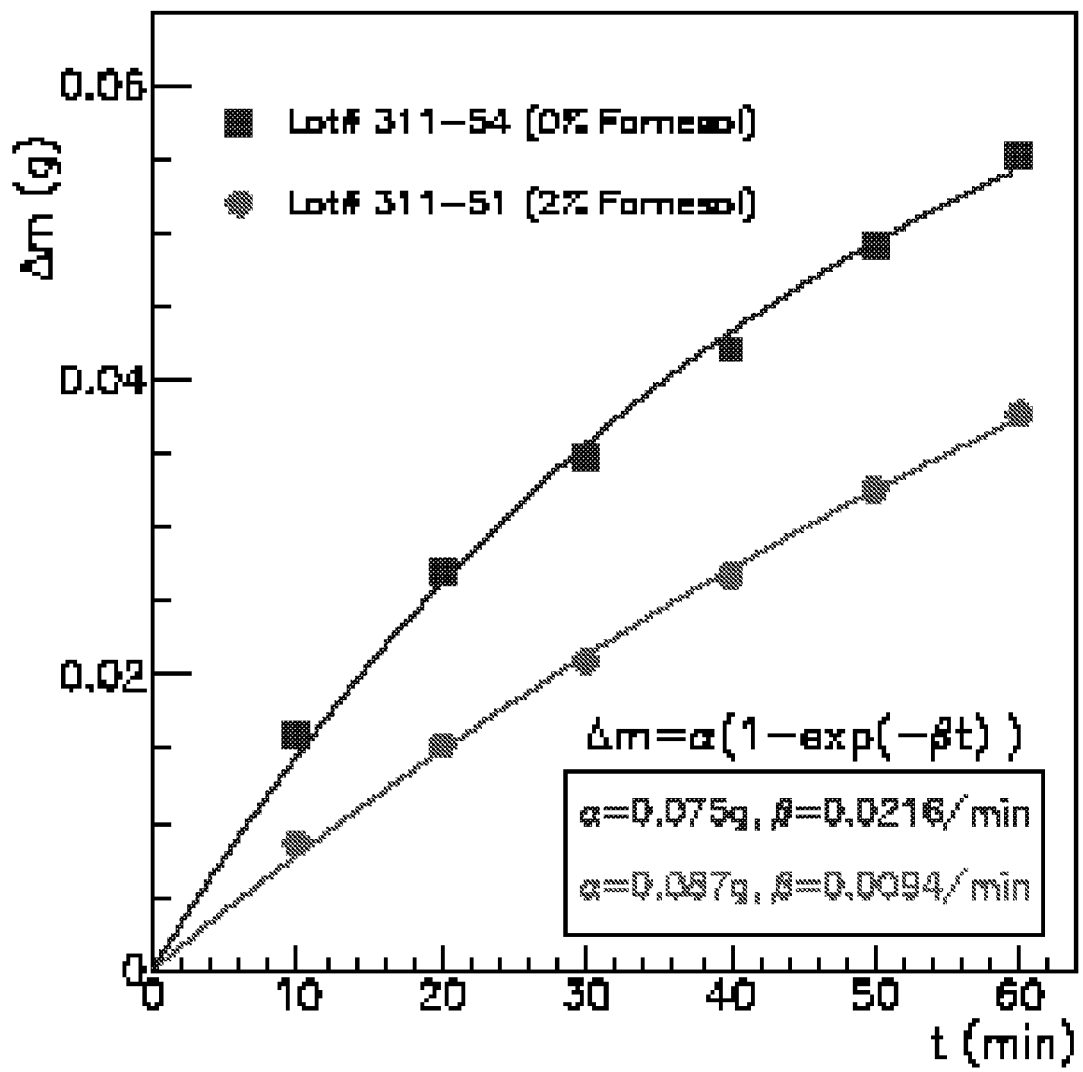
FIG. 1 is a graph reflecting a comparison of the mass lost to evaporation from analgesic formulations with and without farnesol over a one hour period.

A preferred embodiment of the invention is a composition of a deodorizing bacteriostatic agent such as farnesol, one or more topical analgesic volatile organic compounds, and a neuro-sensorial ingredient, to provide a self-preserved, efficacious, odorless, safe and non-irritating topical analgesic formulation.

The preferred neuro-sensorial ingredient is a mixture of pentylene glycol and 4-t-butylcyclohexanol, commercially available as SymSitive 1609. The 4-t-butylcyclohexanol works at the cell communication level directly connecting with a specific neuro-receptor: the TRPV1 thermo-receptor. SymSitive 1609 also acts as a sensiregulator, reducing the calcium flux in the cellular membrane bringing it back to a normal state. In addition SymSitive 1609 helps to increase the skin's tolerance threshold by its regulating action and significantly reduces burning and stinging. SymSitive 1609 produces an immediate effect on heating symptoms and provides an "anti-nerve" hyper-activation which calms over-reaction of the skin and so reduces sensitive symptoms. Other neuro-sensorial ingredients may include Bisabolol and Ginger root extract, and Chamomile extract.

As previously mentioned, farnesol is an organic compound that can reduce the volatility of the topical analgesic actives menthol and camphor, thereby reducing their odor, and also preserves the product. The SymSitive 1609 neuro-sensorial ingredient prevents skin irritation that may be caused by farnesol. These ingredients may be employed in topical analgesic formulations in the form of a cream, gel, lotion, patch, plaster, ointment, solution or spray. The formulations may also contain skin moisturizers, surfactants, carbopol polymers, alcohols, anti-aging and anti-wrinkle ingredients and such as are commonly found in various topical analgesic products, since neither farnesol nor SymSitive 1609 interfere with the usual properties of most of these ingredients. Farnesol is particularly desirable as for use as an odor reducing deodorizing bacteriostatic agent because it has both hydrophilic and hydrophobic portions providing it with detergent-like properties, and micelle-forming ability, so that it can assist in stabilizing an emulsion.

Menthol and camphor are both relatively volatile, having vapor pressures of 8.5 kPa and 86.7 kPa respectively at 25° C. In addition, menthol and camphor have relatively low odor detection thresholds, with camphor reportedly being detectable at concentrations of less than 0.1 parts per million of air. In contrast, the vapor pressure of water is 3.2 kPa and of ethanol 5.9 kPa, and the odor detection threshold of ethanol is about 100 ppm.

EXAMPLE 1

A simple formulation with 0.75% propylene glycol, 8.13% of Novasome (a trademark of IGI Laboratories, Inc.) encapsulated menthol (which contains 1.3% of the total amount of 1-Menthol), 8.13% farnesol, 4% Novemer EC-2 polymer (a sodium acrylates/beheneth-25 methacrylate crosspolymer and hydrogenated polydecene and lauryl glucoside combination thickener, stabilizer and emulsifier sold by Lubrizol Corp.), 0.3% SymSitive 1609, and 78.7% water. This embodiment results in a thick, stable, non-irritating cream with no readily discernable menthol odor even when applied to the skin.

It will be noted in Example 1 that the actual amount of menthol is only 1.3%, since only about 15-17% of the Novasome encapsulated menthol is actually menthol, and the remaining 83-85% is the encapsulation material. Thus, there is only 1.3% menthol by weight, and 8.13% farnesol. This is a moderate to high level of farnesol, and it can be extrapolated that if there was actually 16% menthol instead of 1.3% menthol, the amount of farnesol required to nearly eliminate the menthol odor could be so substantial as to nearly preclude the addition of other ingredients.

A particularly desirable feature of formulations with menthol or camphor as topical analgesic actives, and the use of farnesol, is that each of menthol, camphor, and farnesol is an antibacterial. This means that the formulas need not include additional preservatives. Furthermore, since menthol, camphor and farnesol are all naturally occurring organic molecules, it is entirely possible to create useful analgesic formulations with no artificial ingredients, although these molecules are commonly synthesized rather than extracted from the environment. Avoiding the need for additional preservatives means that formulations can be paraben-free, and this is desirable due to discussion about possible carcinogenicity and estrogenic effects attributable to parabens.

EXAMPLE 2

A more complex formulation that results in a cream having significantly reduced menthol and camphor odor can be created as described below with the following ingredients:

Emulsifiers: Glyceryl Stearate 4%,
  Cetyl Alcohol 2%,
  Stearic Acid 2%,
  Steareth-21 6%

Non Volatile Solvents: Propanediol 10%
Skin Protectant Allantoin 0.1%
Thickener: Carbopol Ultrez-21 0.5%
Skin Moisturizer Aloe Barbadensis Leaf Juice: 0.6%
Actives: Encapsulated Menthol: 0.5%; Encapsulate Material: NOVASOME from (IGI Labs)
  Menthol Racemic 15.5%
  Camphor 11%
Anti-Irritation
Ingredient: SymSitive 1609—Pentylene Glycol and 4-t-Butylcyclohexanol: 0.3%
Solvents: Water 37%,
  Ethanol 5%
Fragrance: 0.5% (Citron, Peppermint oil, Spearmint oil, grapefruit oil, cucumber Asian Pear) each 0.1%
Farnesol 2%
pH Adjuster: Triethanolamine 0.3%

This cream is prepared in a series of steps to maximize the odor reducing capability of the farnesol without requiring more than a moderate amount of this ingredient. The basic requirement is that the volatile camphor and menthol be included in the emulsion of the carrier prior to adding the farnesol. The particularly desired steps of creating the cream from this formula involve preparing a mixture of the oils and emulsifiers as a first phase. Then a second phase is prepared from the solvents and actives and mixed with the first phase and an emulsion is created. Finally, the remaining ingredients, principally the farnesol and fragrances, are added to the emulsion.

A further desirable feature of this formulation is the use of less than 10% ethanol, and in this particular example only 5%. Prior art formulations with substantial concentrations of menthol and camphor have utilized ethanol at concentrations of about 15% which results in products that possess a significantly higher potential for skin sensitization and irritation.

The resulting cream formulation is believed to have a vapor pressure of less than 8 kPa and preferably less than 5 kPa—significantly lower than the vapor pressure of either VOC active. To demonstrate the effectiveness of the formulation at reducing the odor of the actives, informal sensory testing determined that the most noticeable reduction in odor occurred when the concentration of farnesol was increased from 1.5% to 2%. At a 1.5% concentration, there was some reduction of odor, but a 2% farnesol, the odor of camphor and menthol was suppressed to the extent that it was barely detectable. An evaporation rate test was devised to quantify the reduction in volatility and resulting odor. For the purposes of this test, the cream of Example 2 was formulated as described above as Lot#311-51 and also by substituting an additional 2% of water in place of the farnesol as Lot#311-54. The experiment proceeded as follows:

1. Measured the room Temperature and Relative Humidity in the room
  (Results: T=24C, RH=50%)

2. Added 1.0000 g of product into a weighing boat which was previously tared inside the analytical balance.

3. Started the timer and waited for 10 minutes. At 10 minutes recorded the value of the remaining mass on the balance.

4. Recorded mass measurements from the balance every 10 minutes until 60 minutes passed.

| Balance Measurements | | |
|---|---|---|
| Time (min) | Mass (g) (2% farnesol) | Mass (g) (0% farnesol) |
| 0 | 1.0000 | 1.0000 |
| 10 | 0.9914 | 0.9820 |
| 20 | 0.9848 | 0.9731 |
| 30 | 0.9791 | 0.9652 |
| 40 | 0.9733 | 0.9579 |
| 50 | 0.9675 | 0.9508 |
| 60 | 0.9623 | 0.9438 |

Evaporated Mass Calculation ($M_{evaporated}=M_0-M_i$)
($M_0$=1.0000 g. $M_i$=Mass at each time point from 0-60 minutes)

| Time (min) | Mass (g) (2% farnesol) | Mass (g) (0% farnesol) |
|---|---|---|
| 0 | 0.0000 | 0.0000 |
| 10 | 0.0086 | 0.0180 |
| 20 | 0.0152 | 0.0269 |
| 30 | 0.0209 | 0.0348 |
| 40 | 0.0267 | 0.0421 |
| 50 | 0.0325 | 0.0492 |
| 60 | 0.0377 | 0.0562 |

Constructed Graph of "Evaporated VOC Mass (g)" vs. Time (min) as FIG. 1.

The equation that governs the evaporation of VOCs over time is as follows:

$$\Delta m = \alpha(1-\exp(-\beta t))$$

where $\Delta m$ is the evaporated mass, $\alpha$ and $\beta$ are parameters of the fit. Knowing this equation, the experimental data points are fitted with theoretical curves and this provides the values for parameters $\alpha$ and $\beta$ for each curve. See FIG. 1 illustrating $\Delta m$ (t).

The square data points and fitted curve represent the evaporated mass from the Lot#311-54 which is the lot that does not contain farnesol. The round data points and fitted curve represent the evaporated mass from the Lot#311-51 which is the lot that contains 2% farnesol. Looking at the figure of $\Delta m$ (t) it can be seen that the Lot without farnesol evaporates much faster than the Lot with 2% farnesol. In order to calculate and compare the speed of VOC evaporation for both Lots it is possible to examine the derivative of mass over time:

$$dm/dt = d(\alpha(1-\exp(-\beta t))/dt = \alpha\beta e^{t\beta} - \text{VOC Evaporation Rate}(g/hr/cm^2)$$

Figure 2:
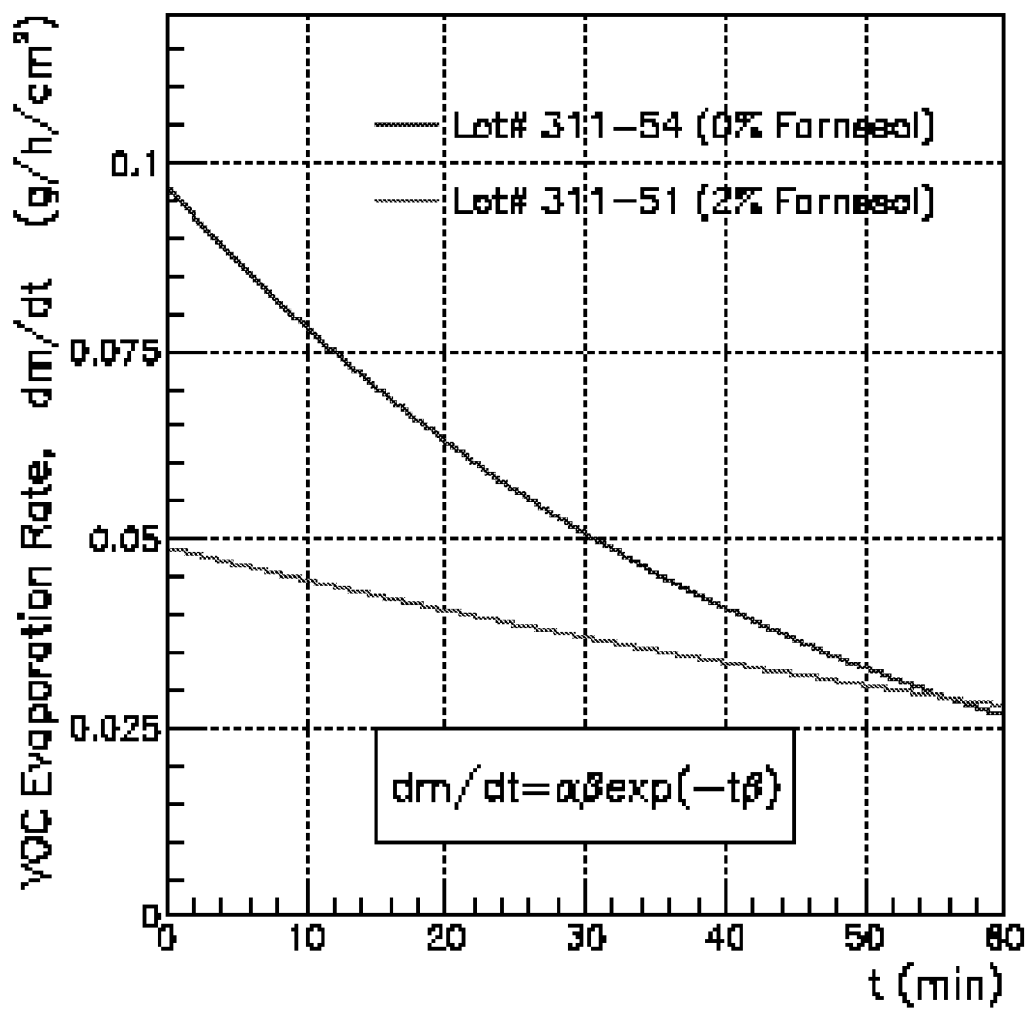
FIG. 2 is a graph reflecting the evaporation rates of the analgesic formulations in FIG. 1.

Then FIG. 2 presents the graph of VOC Evaporation Rate vs. time (dm/dt as a function of time). This graph shows that the VOC Evaporation Rate (a representation of volatility of the VOCs) is significantly lower if 2% farnesol is added into the product. In fact, the initial Evaporation Rate (time=0) is reduced by approximately 50%.

It can also be seen that the evaporation rate over the first hour is reduced by approximately 50% due to the addition of 2% farnesol. So the volatiles in the formula, menthol 16%, camphor 11%, ethanol 5%, water 37%, fragrance 0.5%, and farnesol 2% comprise about 71-72% of the analgesic cream and achieve a VOC evaporation rate of between about 0.03-0.05 grams/hour/cm$^2$. However, the control formulation without farnesol (Lot#311-54) evaporated at a rate of 0.0563 g/hour/cm$^2$ resulting in noticeable odor. It can be appreciated that in alternative formulations with a lower concentration of volatiles, or volatiles with lower vapor pressures, or with higher viscosities, the evaporation rate would be correspondingly lower. In either case, significant odor suppression is realized when the evaporation of volatile ingredients by weight in the first hour is less than 7%, and preferably less than 5%.

In practice, when a cream is applied, the emulsion begins to break down, and the surface area covered by the cream may be several square inches. In addition, the body heat of the user may also hasten vaporization of volatile ingredients. As a result, after application the bonding forces that minimize the evaporation of volatile ingredients are diminished and the odor of menthol or camphor does become slightly detectable after several minutes—although at a significantly less aggressive level than is the case in formulations without adequate farnesol to reduce the volatility or vapor pressure of the product.

An added benefit of reducing the evaporation of menthol and camphor is that the active ingredients remain in contact with the user's skin for a longer time. In fact, testing suggests that users will enjoy therapeutic activity from the active ingredients for about 25-50% longer than if using a formulation without odor suppressing quantities of farnesol.

It can also be noted that more viscous formulations result in less VOC evaporation and the amount of farnesol can be reduced appropriately. Products with very high viscosity (100,000 cPs-1000,000 cPs) hold the VOC ingredients, including the analgesic actives menthol and camphor, inside the formulation and reduce the evaporation rates relative to lower viscosity formulations. In this regard it may be useful to examine additional exemplary formulations for a patch which has relatively high viscosity, a spray which has low viscosity, and a gel which has intermediate viscosity.

EXAMPLE 3

Patch Formulation Example

Polyisobutene B12—15%
Polyisobutene B100—4.5%
Polyethylene Glycol 400—5%
BIO-PSA (Pressure Sensitive Adhesive) 7-4102 Silicone Adhesive (By Dow Corning)—5%
Isopropyl Myristate—25%
Isopropyl Palmitate—25%
Menthol 5%
Camphor 5%
Ethanol 5%
Farnesol 5%
SymSitive 0.5%
Since the carrier of a patch formulation is a solid dough that is typically applied to a fabric backing, it is difficult to formulate products with the maximum levels of both menthol (16%) and camphor (11%) together with the necessary solvents and deodorizing bactericidal agent.

The dough recipes of patch formulations vary widely, although the most common are either hydrogels or hydrophobic polymers such as a rubber polymer, an acrylic polymer or a silicon polymer. Since neither menthol nor camphor are significantly soluble in water, the hydrophobic polymers are quite suitable.

EXAMPLE 4

Topical Spray Example

Menthol—5%
Ethanol—55%
Water—20%
Propylene Glycol 10%
Glycerin—4.5%
Farnesol—5%
SymSitive—0.5%
Other spray formulations with lower concentrations of ethanol may be more effective in minimizing odor and the vapor pressure of the resulting product.

EXAMPLE 5

Transparent Gel Example

Menthol—5%
Ethanol—10%
Propylene Glycol—16%
Water—56.5%
Glycerin—6%
Acrylates/C10-30 Alkyl Acrylate Crosspolymer—0.5%
Triethanolamine—0.5%
HydroxyPropylMethyl Cellulose—0.2%
Farnesol—5%
SymSitive—0.3%
Although in this formulation, the ethanol concentration is higher than preferred to minimize skin irritation and vapor pressure, reformulation to reduce the ethanol level to around 5% should be feasible.

As reflected in the previous examples, the compositions of the present invention may be prepared in a number of forms for topical application to the skin of a patient. For example, the composition may be applied in a gel, cream, ointment, liquid, spray liquid, solidifying emulsion or plaster, or adhesive bandage.

In these embodiments, the topical compositions comprise a dermatologically acceptable carrier. Such a carrier is suitable for topical use that is compatible with the active analgesic ingredients described herein. An effective and safe carrier generally varies from about 50% to about 97% by weight of the compositions.

Useful topical compositions can be formulated as solutions, as in Example 4. Solutions typically include an aqueous or organic solvent (e.g., from about 50% to about 97% of one or more cosmetically acceptable aqueous or organic solvents). Examples of suitable organic solvents include: propylene glycol, polyethylene glycol (200-600), polypropylene glycol (425-2025), glycerol, 1,2,4-butanetriol, sorbitol esters, 1,2,6-hexanetriol, ethanol, and mixtures thereof.

Solutions may be formulated as an emollient. Such compositions preferably contain from about 2% to about 50% of one or a combination of emollients. As used herein, "emollients" refer to materials used for the prevention or relief of dryness, as well as for the protection of the skin. A wide variety of suitable emollients are known and may be used herein, such as allantoin, aloe, and tocopheryl acetate. Sagarin, Cosmetics, Science and Technology, 2nd Edition, Vol. 1, pp. 32-43 (1972) and the International Cosmetic Ingredient Dictionary and Handbook, eds. Wenninger and McEwen, pp. 1656-61, 1626, and 1654-55 (The Cosmetic, Toiletry, and Fragrance Assoc, Washington, D.C., 7th Edition, 1997) (hereinafter "ICI Handbook") contain numerous examples of suitable materials.

A lotion is an oil-in-water emulsion that can be made from a solution containing an emollient. Lotions typically comprise from about 1% to about 20% of at least one emollient and from about 50% to about 80% of water. Another type of emulsion that may be formulated from a solution containing an emollient is a cream. A cream may be either a water-in-oil emulsion or an oil-in-water emulsion and typically comprises from about 5% to about 50% of one or more emollients and from about 40% to about 85% of water.

If the carrier is an emulsion, from about 1% to about 10% of the carrier comprises one or more emulsifiers such as surfactants, detergents, or co-solvents. In the above examples, glyceryl stearate, cetyl alcohol, stearic acid, and Steareth 21 (polyethylene glycol) all function as emulsifiers. Depending upon the composition of the carrier, emulsifiers may be nonionic, anionic or cationic. Suitable emulsifiers are disclosed in, for example, McCutcheon's Detergents and Emulsifiers, North American Edition, pp. 317-324 (1986), and the ICI Handbook, pp. 1673-1686. Multi-phase emulsion compositions, such as the water-in-oil-in-water type, may also be used. In general, such single or multiphase emulsions contain water, emollients, and emulsifiers as ingredients.

With respect to the principal volatile analgesic actives of menthol and camphor, ethanol is the principal solvent used in the foregoing example formulations. Other solvents may include propanediol, propylene glycol, dimethyl isosorbide, polyethylene glycol 300, polyethylene glycol 400, polysorbate 20, and/or polysorbate 80.

Yet another type of product that may be formulated from a solution containing an emollient is an ointment. An ointment can comprise a simple base of animal or vegetable oils or semi-solid hydrocarbons. An ointment may comprise from about 2% to about 10% of one or more emollients plus up to about 2% of one or more thickening agents. A more complete disclosure of thickening agents or useful viscosity increasing agents can be found in Sagarin, Cosmetics, Science and Technology, 2nd Edition, Vol. 1, pp. 72-73 (1972) and the ICI Handbook pp. 1693-1697.

Useful topical compositions can also be formulated as a gel (e.g., an aqueous, alcohol, alcohol/water, or oil gel using at least one suitable gelling agent), as in Example 5. Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprise between about 0.1% and 5%, by weight, of such gelling agents.

In one embodiment the active ingredients are impregnated in a patch or fabric for prolonged contact with the skin. A patch is commonly manufactured by adding the active ingredients to a hydrogel or rubber dough. A typical hydrogel dough would comprise a gel forming polymer such as guar gum, maltodextrin, carboxymethyl cellulose or other polysaccride or cellulosistic polymer; or a synthetic polymer such as polyacrylide and its cogeners. A typical rubber-type dough could contain polyisobutylenes, styrene-isoprene-styrene block co-polymer, a rosin or resin tackifier and an oil or liquid paraffin plasticizer. Handbook of Cosmetic Science & Technology, (A. Barel, M. Paye and H. Maibach eds.), Marcel Dekker Ltd., 2001, pp. 233-240. Examples of the rubber polymer may include a styrene-isoprene-styrene block copolymer, polyisobutylene, a styrene-butadiene-styrene block copolymer, a styrene-butadiene rubber, or an isoprene rubber. Doughs can also be made from acrylic polymers or silicon polymers, so long as the formulation creates sufficient matrices to hold the active and ancillary ingredients being delivered to surface of the user's skin.

Liposomal formulations are also useful to encapsulate volatile active ingredients. In one embodiment, the peptide and/or the pigment are contained within the liposome. Examples of liposomes are unilamellar, multilamellar, and paucilamellar liposomes, which may or may not contain phospholipids. Compositions and uses of topically applied liposomes are described in Mezei, M., "Liposomes as a Skin Drug Delivery System", Topics in Pharmaceutical Sciences (D. Breimer and P. Speiser, eds.), Elsevier Science Publishers B. V., New York, N.Y., 1985, pp. 345-358, PCT Patent Application No. WO96/31194, Niemiec, et al, 12 Pharm. Res. 1184-88 (1995), and U.S. Pat. No. 5,260,065. Methods of preparing liposomes are well known in the art.

Useful topical compositions may contain, in addition to the aforementioned components, a wide variety of additional oil-soluble materials and/or water-soluble materials conventionally used in compositions for use on skin at their art-established levels. Various other materials may also be present in the compositions useful in the subject invention. These include adsorbants, humectants, proteins and polypeptides, preservatives and pH adjusting agents. Examples of such agents are disclosed in the ICI Handbook, pp. 1650-1667.

All publications, patent, and patent documents are incorporated by reference herein as though individually incorporated by reference. Although preferred embodiments of the present invention have been disclosed in detail herein, it will be understood that various substitutions and modifications may be made to the disclosed embodiment described herein without departing from the scope and spirit of the present invention as recited in the appended claims.

What is claimed is:

1. A odor suppressing composition comprising:
   a) from about 1.0% to 20%, by weight, of deodorizing bacteriostatic agent;
   b) from about 1.25% to about 70%, by weight, of one or more volatile organic analgesics selected from the group of menthol, camphor, methyl salicylate, and combinations of thereof;
   c) at least about 0.1% by weight of a neuro-sensorial ingredient, wherein said ingredient is selected from the group consisting of: a mixture of 4-t-butylcyclohexanol and pentylene glycol, bisabolol, ginger root extract and chamomile extract; and
   d) a topical carrier.

2. The odor suppressing composition of claim 1, wherein said deodorizing bacteriostatic agent is selected from the group of farnesol, 2-methyl 5-cyclohexylpentanol, dimethyl phenyl 2-butanol and combinations thereof.

3. The odor suppressing composition of claim 1, wherein said deodorizing bacteriostatic agent comprises at least 1.5% by weight of farnesol.

4. The odor suppressing composition of claim 1, wherein at least a portion of said volatile organic analgesic is encapsulated with an encapsulate material.

5. The odor suppressing composition of claim 4, wherein the encapsulate material encapsulating the volatile organic analgesic compound is comprised of water, menthyl lactate, diisopropyl adipate, glyceryl stearate, ethoxydiglycol, glyceryl dilaurate, polysorbate 80, PEG-150 stearate, cetyl alcohol, soya sterol, phenoxythanol, methylparaben, glycerin, disodium EDTA, xanthan gum.

6. The odor suppressing composition of claim 1, wherein said topical carrier is selected from the group consisting of water-in-oil or oil-in-water emulsion, gel, patch, plaster, ointment, solution or spray.

7. The composition according to claim 1, wherein the composition has a viscosity of from about 10,000 to about 1,000,000 centipoise, and wherein the water is present in an amount from about 30% to 60%.

8. The composition according to claim 1, wherein the composition contains less than 10% ethanol.

9. The composition according to claim 1, wherein the composition has a vapor pressure of less than 8 kPa.

10. The composition according to claim 1, wherein the composition is substantially free of artificial preservatives.

11. The composition according to claim 1, wherein the composition is substantially free of parabens.

12. The composition according to claim 1, wherein the composition has a relatively low evaporation rate such that after being exposed for one hour at 25° C., less than 7% by weight of the volatile ingredients have evaporated.

13. The composition according to claim 1, wherein the composition is an anhydrous formulation in the form of a patch or an ointment.

14. The composition according to claim 1, wherein the neuro-sensorial ingredient of the composition comprises at least 0.25% by weight of a mixture of 4-t-butylcyclohexanol and pentylene glycol.

15. The composition according to claim 7, wherein the composition is in the form of a cream having at least 4% menthol and 2% farnesol.

16. The composition according to claim 1, wherein the composition further comprises oils and emulsifiers and solvents and is in the form of an emulsion created by forming a first phase containing oils and emulsifiers and mixing this with a second phase formed of solvents and volatile organic analgesics, and the deodorizing bacteriostatic agent is added to the composition after the emulsion has been created.

17. The composition according to claim 16, wherein the deodorizing bacteriostatic agent of the composition comprises farnesol in an amount of at least 2% by weight.

18. The composition according to claim 1, wherein the composition is in the form of a patch comprising a styrene-isoprene-styrene block co-polymer dough having menthol of at least 5% by weight as a volatile organic analgesic, farnesol in an amount of at least 2% by weight as a deodorizing bacteriostatic agent and no more than 10% by weight of ethanol.

19. The composition according to claim 18, wherein the composition has a vapor pressure of less than 8 kPa.

20. The composition according to claim 1, wherein the composition is in the form of a gel comprising a gelling agent, menthol of at least 5% by weight as a volatile organic analgesic, farnesol in an amount of at least 2% by weight as a deodorizing bacteriostatic agent and no more than 10% by weight of ethanol.

* * * * *